United States Patent [19]

Hagiwara

[11] Patent Number: 5,698,212
[45] Date of Patent: Dec. 16, 1997

[54] ANTIMICROBIAL POLYMER COMPOSITION

[75] Inventor: Zenji Hagiwara, Kusatsu, Japan

[73] Assignees: Hagiwara Research Corporation, Shiga-Ken; Japan Electronic Materials Corporation, Hyogo-Ken, both of Japan

[21] Appl. No.: 614,251

[22] Filed: Mar. 12, 1996

[30] Foreign Application Priority Data

Mar. 14, 1995 [JP] Japan ................... 7-080881

[51] Int. Cl.$^6$ .............................. A01N 25/26; A01N 25/08
[52] U.S. Cl. ................... 424/409; 424/419; 424/421; 514/772.3; 514/772.4
[58] Field of Search ................ 424/409, 772.4; 514/772.3

[56] References Cited

U.S. PATENT DOCUMENTS

| | | | |
|---|---|---|---|
| 1,930,492 | 8/1933 | Zellman | 424/618 |
| 3,159,536 | 12/1964 | Marotta | 424/421 |
| 4,006,175 | 2/1977 | Tormin et al. | 556/10 |
| 4,525,410 | 6/1985 | Hagiwara et al. | 428/198 |
| 4,593,040 | 6/1986 | Adam et al. | 514/395 |
| 4,929,431 | 5/1990 | Hagiwara et al. | 423/328 |
| 4,959,268 | 9/1990 | Hagiwara et al. | 428/403 |
| 5,244,667 | 9/1993 | Hagiwara et al. | 424/409 |
| 5,298,252 | 3/1994 | Hagiwara et al. | 424/408 |
| 5,468,738 | 11/1995 | Okabayashi et al. | 514/63 |

*Primary Examiner*—Peter F. Kulkosky
*Attorney, Agent, or Firm*—Roylance,Abrams,Berdo & Goodman, L.L.P.

[57] ABSTRACT

The present invention provides a novel antimicrobial polymer composition having superior weatherability and discoloration resistance to those of the prior art.

The present invention provides an antimicrobial polymer composition comprising a polymer and an antimicrobial composition having an antimicrobial coat of an aluminosilicate on the surface of silica gel, wherein said aluminosilicate containing antimicrobial metal ions, characterized in that said antimicrobial polymer composition further comprises thiabendazole.

7 Claims, No Drawings

ANTIMICROBIAL POLYMER COMPOSITION

FIELD OF THE INVENTION

The present invention relates to an antimicrobial polymer composition.

Background of the Invention

An antimicrobial polymer composition comprising a polymer and an antimicrobial composition having an anti-microbial coat of an aluminosilicate on the surface of silica gel, wherein said aluminosilicate containing antimicrobial metal ions, such as silver, copper and zinc, is disclosed in the U.S. Pat. Nos. 5,244,667 and 5,298,252.

Since said antimicrobial composition is effective against common fungi and also exhibits excellent biocidal activity against mildew, research and development leading to new applications have been carried out. Furthermore, research and development of an antimicrobial polymer composition comprising said antimicrobial composition is also carried out and some uses have been developed.

However, if said silica gel based antimicrobial composition is added to a polymer and molded under heating, it is known that an undesirable discoloration or coloring occurs in some polymers under certain processing conditions, due to an interaction of antimicrobial composition with polymer or an interaction of antimicrobial composition with additives or catalyst contained in a polymer.

Furthermore, an antimicrobial polymer molding may discolor or degrade with time and an economical value may be damaged. In some polymers, a discoloration is accelerated by a radiation of sunlight or ultraviolet light.

Many researches have been carried out to resolve the defects of the prior antimicrobial polymer composition containing the above mentioned antimicrobial composition. A discoloration resistance and a weatherability are improved, however, they are not satisfactory, yet. The technology that can prevent a coloration which occurs during blending or molding under heating or a variety of the molded article with time has not been developed.

Accordingly, it is desired to develop a novel technology that can prevent a discoloration or coloration of the antimicrobial polymer composition and improve the weatherability. The main object of the present invention is to provide a novel antimicrobial polymer composition which resolves the above mentioned defects of the prior art.

SUMMARY OF THE INVENTION

The present invention relates to an antimicrobial polymer composition comprising a polymer and an antimicrobial composition having an antimicrobial coat of an aluminosilicate on the surface of silica gel, wherein said aluminosilicate containing antimicrobial metal ions, characterized in that said antimicrobial polymer composition further comprises thiabendazole. Furthermore, the present invention relates to said antimicrobial polymer composition further comprising inorganic additives.

The antimicrobial polymer composition of the present invention has an excellent biocidal ability, a discoloration resistance and a weatherability and shows less variation with time.

Detail Description of The Invention

The present inventor has found that a selection of an additive is important to improve a heat resistance, a weatherability and a light-resistance and minimize a discoloration of the antimicrobial polymer composition comprising a polymer and silica gel based antimicrobial composition.

As the result of research of additives, the inventor has found that thiabendazole (hereinafter referred as TBZ) improves a heat resistance, a weatherability and minimizes a discoloration of the antimicrobial polymer composition comprising a polymer and an antimicrobial composition having an anti-microbial coat of an ahminosilicate on the surface of silica gel, wherein said aluminosilicate containing antimicrobial metal ions. In the present specification, an antimicrobial composition having an antimicrobial coat of an aluminosilicate on the surface of silica gel, wherein said aluminosilicate containing antimicrobial metal ions is occasionally referred to as silica gel based antimicrobial composition. Furthermore, an addition of the after mentioned inorganic additives further improves physical properties of the obtained antimicrobial polymer composition.

The present invention provides a novel antimicrobial polymer composition having superior weatherability and discoloration resistance to those of the prior art.

The present invention provides an antimicrobial polymer composition comprising a polymer and an antimicrobial composition having an antimicrobial coat of an aluminosilicate on the surface of silica gel, wherein said aluminosilicate containing antimicrobial metal ions, characterized in that said antimicrobial polymer composition further comprises thiabendazole.

Preferably, the antimicrobial metal ions are silver ions or silver ions and one or two metal ions selected from the group consisting of zinc ions and copper ions. A content of the antimicrobial composition is preferably at least 0.2% by weight of the antimicrobial polymer composition to provide satisfactory antimicrobial effects, A content of TBZ is preferably at least 0.03% by weight of the antimicrobial polymer composition to provide good weatherability and discoloration resistance.

A content of the silver ions is preferably at least 0.3% by weight of the antimicrobial composition to provide a good antimicrobial rate.

An antimicrobial polymer composition of the present invention may further comprise at least one additive selected from the group consisting of titanium dioxide, zirconium oxide, cerium oxide and layer silicates. Such as antimicrobial polymer composition provides a remarkably improved weatherability and discoloration resistance. A thermoplastic resin and a thermosetting resin are preferably used as a polymer of the antimicrobial polymer composition of the present invention. A natural resin, a semi-synthetic resin and a regenerated resin can be used as a polymer of the antimicrobial polymer composition of the present invention.

To prepare the antimicrobial polymer composition of the present invention, an amorphous antimicrobial composition having an antimicrobial coat of an aluminosilicate on the surface of micro pores and/or macro pores of silica gel, wherein said aluminosilicate contains silver ions and one or two optional metal ions selected from the group consisting of zinc and copper is used as an antimicrobial composition. Said antimicrobial composition may contain non-biocidal metal ions having valences of 1 to 3 or ammonium ions.

The process for preparing the amorphous antimicrobial composition is well known as disclosed in U.S. Pat. No. 5,244,667 and briefly stated below.

The process comprises a first step of chemically treating a porous silica gel with an alkali solution and an aluminate solution and then forming an antimicrobial coat on the thus-treated surface of the silica gel and the second step of treating with a salt solution comprising at least one type of antimicrobial metal ion to allow antimicrobial metal ions [Ag+ and optional $Zn^{2+}$ and/or $Cu^{2+}$] to be retained in the aluminosilicate coat so that an antimicrobial coat is formed. In the first step, aluminic acid ions [$Al(OH)_4^-$; $AlO_2.2H_2O$] react with $Si(OH)_4$ [$SiO_2.2H_2O$ as a monomer] present on a surface of pores (micro pores and/or macro pores) in the silica gel to form negatively charged aluminosilicate ions.

A firm ionic bond is formed between aluminosilicate ions and porous silica gel so that the release of the former from the later gel body is completely prevented. In the second step, an ion-exchange treatment is carried out in order to retain antimicrobial and/or microbial ion of Ag+ and optional $Zn^{2+}$ and $Cu^{2+}$ ions in the thin aluminosilicate layer. By performing above process, antimicrobial metal ions are exchanged with ion-exchangeable metal ions in the aluminosilicate layer and thus formed antimicrobial layer is fixed strongly on the surface of the silica gel pores. Through the above procedure, the antimicrobial composition used in the present invention is prepared.

A predetermined amount of necessary antimicrobial metal ions in the antimicrobial composition is able to present in the form of single metal ion or composite metal ions, i.e. $Ag^+$, $Ag^+$—$Zn^{2+}$, $Ag^+$—$Cu^{2+}$, and $Ag^+$—$Zn^{2+}$—$Cu^{2+}$. In addition to the above metal ions, the antimicribial composition may contain non-biocidal metal ion having valences of 1 to 3, such as monovalent alkali metal ions, nickel and other alkaline earth metal ions with divalent, trivalent rare earth elements [lanthanoid elements: Ln3+, elements having an atomic number of from 58 to 71, 21 (Sc), 39(Y) and 57(La)] and zirconium (in a form of zirconyl:$ZrO^{2+}$). Furthermore, the antimicrobial composition may contain ammonium ions, such as $NH_4^+$, $C_7H_{15}N_2^+$, $C_3H_{16}N^+$, $Me_4N^+$ (TMA:tetramethylammonium ion), $Et_4N^+$ (TEA:tetraethylammonium ion), and $Pr_4N^+$ (TPA:tetrapropylammonium ion).

The antimicrobial composition used in the present invention is prepared by the above-mentioned process and comprises a silica as a major component thereof. It comprises preferably at least 70 wt. % of $SiO_2$ and 15 wt % or less of alumina ($Al_2O_3$). It further comprises antimicrobial metal ions, such as Ag, Zn and Cu, and non-biocidal metal ions having a valence of 1 to 3. Such an antimicrobial composition has a large SSA, typically 350–600$m^2$/g, leading to high porous. A form of the antimicrobial composition is not restricted and it is preferably used as a fine powder or a ground particle.

The antimicrobial composition used in the present invention exhibits an excellent antimicrobial effect against fungi and good mildewcidal effects.

TBZ is used to prevent a discoloration of the antimicrobial polymer composition and to improve a weatherability. The chemical formula of TBZ is 2-(4-thiazoyl)-benzimidazole, $C_{10}H_{17}N_3S$, and available from MELK Co. Ltd. TBZ is a pale yellow powder and has a molecular weight of 201.25, a melting point of 300° C., a specific gravity of 1.44 and a decomposition temperature of 700° C. TBZ has an imprimatur as a food additive from FDA (Food & Drug Administration in the U.S). TBZ has $LD_{50}$s of 3600 mg/kg(mouse) and 3800 mg/kg(rabbit) and has a large safety to an organism. TBZ is used as a mildewcide, however it is known that TBZ has no biocidal ability.

It is unknown that TBZ prevents a discoloration, a coloration with time of antimicrobial polymer composition comprising silica gel based antimicrobial composition, and improve a weatherability of the antimicrobial polymer composition. The inventor investigated many kinds of weatherability modifiers, compounding ingredients, antioxidants, brighteners and pigments and found that TBZ has the strongest effects among them. Although, TBZ is an organic compound containing sulfur, there is no tendency to inhibit an antimicrobial ability of the silica gel based antimicrobial composition comprising silver ions.

Regarding to many kinds of polymers, such as polypropylene, low density polyethylene, high density polyethylene and ABS resin, a discoloration and variation with time of the compositions can be prevented by an addition of TBZ at the level from 0.03 to 3% by weight of the polymer. Furthermore, an antimicrobial ability of the polymer composition against fungi is not changed by the addition of TBZ. Accordingly the obtained antimicrobial polymer composition represents excellent antimicrobial ability.

The present invention further provide an antimicrobial polymer composition comprising polymer, at least 0.2 wt % of before mentioned antimicrobial composition, at least 0.03 wt % of TBZ and at least one additive selected from the group consisting of titanium dioxide($TiO_2$), zirconium oxide ($ZrO_2$), cerium oxide($CeO_2$) and layer silicate. A discoloration of the composition and a weatherability are improved significantly by an opacifying property thereof. The layer silicate include talc; $Mg_3(Si_4O_{10})(OH)_2$, mica such as Muscovite: $KAl_2(AlSi_3O_{10})(OH)_2$, phlogopite: $KMg_3(AlSi_3O_{10})(OH)_2$, Lepidolite: $K(Li_2,Al)(Si_4O_{10})(F, OH)_2$, Margarite: $CaAl_2(Al_2Si_2O_{10})(OH)_2$, and Vermiculite (($CaMg)_{x/2}(Mg, Fe, Al)_3(Al, Si)_4O_{10}(OH)_2.mH_2O$; smectite such as Monmorillonite: $Na_x(Al_{2-x})Mg_x(Si_4O_{10})(OH)_2.mH_2O$, Saponite: $Ca_{x/2}Mg_3(Al_xSi_{4-x}O_{10})(OH)_2.mH_2O$, and Sauconite: $M_x(Zn, Mg)_3(Al_xSi_{4-x}O_{10})(OH)_2.mH_2O$.

An explanation as to the polymer used in the present invention is provided in the following.

Both halogenated and non-halogenated organic polymers may be used in preparing the antimicrobial polymer composition of the present invention. Non-halogenated organic polymers used in the present invention are not limited to any particular kinds and may be synthetic or semi-synthetic and include the following: thermoplastic synthetic polymers such as polyethylene, polypropylene, polystyrene, polyamide, polyesters, polyvinyl alcohol, polycarbonates, polyacetals, ABS resins, acrylic resins, fluorine resins, polyurethane elastomers and polyester elastomers; thermosetting synthetic polymers such as phenolic resins, urea resins, melamine resins, unsaturated polyester resins, epoxy resins and urethane resins; and regenerated or semi-synthetic polymers such as rayon, cuprammonium rayon, cellulose monoacetate, cellulose diacetate and cellulose triacetate. If a strong antimicrobial and/or microbicidal effect is necessary, SSA of the polymer composition is preferably increased and is preferably foamed or otherwise shaped into a net, a fiber, etc. From this viewpoint, the preferred polymers are organic or fiber-forming polymers such as synthetic polymers exemplified by nylon 6, nylon 66, polyvinyl alcohol, polyethylene terephthalate, polybutylene terephthalate, polyacrylonitrile, polyethylene, polypropylene and copolymers thereof, and regenerated or semi-synthetic polymers exemplified by rayon, cuprammonium rayon, cellulose monoacetate, cellulose diacetate and cellulose triacetate. Halogenated organic polymers that can be used in the present invention also are not limited to any particular kinds and may be exemplified by polyvinyl chloride and polyvinylidene chloride.

The time at which the silica gel based antimicrobial composition is added to the polymer and the method by which it is added are not limited in any particular way in the present invention. For example, the antimicrobial composition may be mixed with a starting monomer and the mixture is then polymerized. In another method, the composition may be mixed with a reaction intermediate and the mixture is then polymerized. Alternatively, the composition may be mixed with the complete polymer, if desired, the silica gel based antimicrobial composition is mixed with polymer pellets or a master batch is prepared from a polymer composition containing the antimicrobial composition and the mixture or master batch is shaped to a desire form. In still another method, the antimicrobial composition is mixed with a molding dope, for example, a spinning solution. The procedure of these method is hereinafter referred to simple as "mixing the silica gel based antimicrobial composition with a polymer or adding it to the polymer".

A suitable method may be adopted taking into account the characteristics of the polymer used and process conditions. In ordinary cases, the silica gel based antimicrobial composition is desirably mixed with the polymer just before molding. However, in order to insure more efficient dispersion of the silica gel based antimicrobial composition, it may be mixed with a monomer. When a predetermined amount of the antimicrobial composition is to be added to a polymer, the atmosphere (e.g. an oxidizing atmosphere such as the air or an inert gas atmosphere such as $N_2$ or $CO_2$), the temperature for mixing or the mixing time may be held at preferred conditions in accordance with the specific characteristics of the polymer used. The silica gel based antimicrobial composition is preferably used in an amount of 0.2–20 wt % of the total weight of the polymer composition. If the content of the silica gel based antimicrobial composition is less than 0.2 wt % of the total weight of the polymer composition, the antimicrobial and/or microbicidal activity of the polymer composition is often unsatisfactory against common bacteria and fungi. If the content of the silica gel based antimicrobial composition is more than 20 wt % of the total weight of the polymer composition, the antimicrobial and/or microbicidal activity of the resulting polymer composition is saturated and any further addition of the silica gel based antimicrobial composition will not contribute to an improved antimicrobial and/or microbicidal action. Furthermore, an excessive addition of the silica gel based antimicrobial composition has the potential to deteriorate the physical properties of the obtained polymer composition.

The particle size of the silica gel based antimicrobial composition that is advantageously used to produce the antimicrobial polymer composition of the present investigation is discussed below.

While there is no particular limitation on the particle size of the silica gel based antimicrobial composition, there is of course a preferred range depending on the specific use of the product. For example, particles of the antimicrobial composition with sizes of 548–149 micro meters (30–100 mesh) can be used for mixing with the polymer but in order to insure more uniform dispersion in the polymer, smaller particles, for example, those having sizes of 200–300 mesh or much finer particles with sizes of from several micro meters to less than a hundred micro meters, may be used.

The particle size of the antimicrobial composition may be adjusted by selecting a preferable mill, such as JET mill, depending on a purpose of the product. When the antimicrobial polymer composition of the present invention is a shaped part having a certain thickness, for example, in the case where it is to be applied to various types of containers, pipes, granules of filaments of large denier, the silica gel based antimicrobial composition may have particle sizes of larger than several tens or several hundreds micro meters. If, on the other hand, the polymer composition is tube shaped into fibers of fine denier or thin films, the particle size of the silica gel based antimicrobial composition is desirably small. For example, in the case of manufacturing fibers for apparel, particle sizes of not more than 5 micro meters are preferred.

In addition to the silica gel based antimicrobial composition, the antimicrobial polymer composition of the present invention may contain other ingredients that are commonly used in the art. Examples of such secondary ingredients include: polymerization catalysts, stabilizers, weathering (lightfast) agents, compounding agents, antioxidants, activators, matting agents, foaming agents, flame retardants, modifiers, brighteners, pigments (colorants), inorganic or organic fillers, various plasticizers and lubricants. These additives may be incorporated as required. The antimicrobial polymer composition of the present invention may also contain liquids or organic solvents. When said composition is to be used as a shaped part, its shape and size are in no way limited. In order to provide the shaped part with an antimicrobial and/or microbicidal activity, it may be imparted to the whole part of the polymer, or if desired, to only part thereof. When the microbicidal polymer composition of the present invention is shaped part, its microbicidal action is considered to be largely dependent on the silica gel based antimicrobial composition present near the surface of the shaped part, so it may be advisable to provide the shaped part with a multilayer structure and treat its outer layer to acquire a microbicidal activity. In the case of fibers, a core/sheath yarn may be prepared by a known conjugate fiber spinning technique, with the antimicrobial polymer composition of the present invention being used as the sheath component.

The antimicrobial polymer composition of the present invention comprising the silica gel based antimicrobial composition at least 0.2% by weight of the antimicrobial polymer composition and TBZ at least 0.03% by weight of the antimicrobial polymer composition keeps excellent biocidal ability against fungi for a long time and shows good weatherability. It shows little coloration or discoloration over time. Furthermore, since the antimicrobial polymer composition of the present invention has a good water-resistance, it shows little change in water or hot water over time.

By incorporating effective amount of at least one additive selected from the group consisting of titanium dioxide, zirconium oxide, cerium oxide and layer silicate into the present antimicrobial polymer composition, a discoloration of the antimicrobial polymer composition is further lowered and a weatherability is further improved. These advantageous effects are obtained by an addition at a few percentage by weight of antimicrobial polymer composition.

TBZ improves a discoloration and a weatherability and causes no adverse effects on antimicrobial ability of the silica gel based antimicrobial composition. Furthermore, the silica gel based antimicrobial composition causes no adverse effects on mildewcidal ability of TBZ. Accordingly, an incorporation of silica gel based antimicrobial composition and TBZ causes no inconvenience. A mildewcidal ability is strengthen by the incorporation, because both have mildewcidal ability.

The antimicrobial polymer composition of the present invention has the following advantages:

(a) The antimicrobial polymer composition comprising silica gel based antimicrobial composition, TBZ and polymer has an excellent discoloration resistance and weatherability.

(b) An incorporation of at least one additive selected from the group consisting of titanium oxide, zirconium oxide, cerium oxide and layer silicate to the present antimicrobial polymer composition further improves a discoloration resistance and a weatherability.

(c) The antimicrobial polymer composition in the above (a) or (b) have an excellent antimicrobial ability against fungi.

(d) The antimicrobial polymer composition has an excellent mildewcidal ability. Since it contains TBZ and silica gel based antimicrobial composition, both of which have mildewcidal ability.

The present invention is described in detail by working examples, however they are not intended to restrict the scope of the present invention.

An antimicrobial ability of the antimicrobial polymer composition was measured by the following "Drop method."

1) The tested bacterium or fungus

*Escherichia coli* (IFO 12734)

*Staphylococcus aureus* (IFO 12732)

*Aspergillus niger* (IFO 4407)

2) Preparation of the suspension of the tested bacterium or fungus

The cells of *Escherichia coli* or *Staphylococcus aureus* that had been cultivated in Nutrient Agar (Oxoid) for 18–24 hours were suspended in sterile phosphate buffer at a concentration of from $10^5$ to $10^6$ cells/ml. To prepare a cell suspension of *Aspergillus niger*, the conidia of the *Aspergillus niger* that had been cultivated in a potato dextrose agar medium (available from Eiken Chemical Corp.) at 25° C. for 7–10 days were suspended in sterile 0.005% dioctyl sodium sulfosuccinate aqueous solution and filtered with sterile gauze to prepare a suspension at a concentration of $10^6$ cells/ml.

3) Medium and cultivation condition

For *Escherichia coli* or *Staphylococcus aureus*
   Mueller Hinton Medium (Difco): 35° C. for 2 days For *Aspergillus niger*
   Sabouraud Dextrose Agar (Difco): 25° C. for 7 days 4) Preparation of the test piece 25 mm×25 mm×1.5 mm (thickness) sized test piece was cleaned with alcohol-impregnated cotton and air-dried. The obtained test piece was provided to the test.

5) Test procedure 0.3 ml of the suspension of *E. coli*, *S. aureus* or *A. niger* was dropped on a surface of the test piece. The test piece was stood for a given time. At 8, 12 and 24 hours later, a number of viable cells was counted by mixed plate culture method. In the tables 1–5, "<10" represents that a number of viable cells was lower than a limit of detection. The number represented in the tables 1–5 is a number of viable cells per test piece.

EXAMPLE 1

In this example, antimicrobial low density polyethylene (LDPE) compositions comprising antimicrobial composition at less than 1% by weight were prepared and the antimicrobial ability thereof were measured.

Sumikasen F101-3 available from Sumitomo Chemical Co. Ltd. is used as LDPE. Bactenon AZ, which is a powdery antimicrobial composition having an antimicrobial coat of aluminosilicate on the surface of silica gel and said antimicrobial coat contains metal ions, is used as the silica gel based antimicrobial composition. Its water content was controlled below 1% by weight. A predetermined amount of Bactenon AZ, TBZ, zirconia($ZrO_2$) and talc were mixed with the LDPE. The obtained mixture was melted and kneaded at 195°–210° C. and molded.

The moldings were cut into test pieces sized 25 mm×25 mm and 1.5mm thick. In the test pieces 1-1, 1-2 and C-1, Bactenon AZ containing 3.51% of Ag, 1.96% of Zn and 0.95% of Na and having 2.8 micro meters of Dav was used. Dav means an averaged diameter. In the test piece 1-3, Bactenon AZC containing 3.82% of Ag, 1.13% of Zn, 1.24% of Cu and 0.89% of Na and having 3.2 micro meters of Dav was used. The compositions of the prepared antimicrobial LDPE compositions are shown in the Table 1, where the test piece C-1 is a comparative example and 1-BL is a blank test piece containing no antimicrobial composition.

The antimicrobial LDPE compositions of the present invention show a good antimicrobial ability against *S. aureus*. TBZ, zirconia and talc do not interfere an antimicrobial ability of Bactenon AZ.

TABLE 1

| Sample No. | Composition of molded antimicrobial polymer | Fungus | Number of viable cells (hrs.) 0 | 12 | 24 |
|---|---|---|---|---|---|
| 1-1 | LDPE-Bactenon AZ, 0.7%-$ZrO_2$, 2%-TBZ, 0.5% | *S. aureus* | $9.4 \times 10^5$ | 0 | — |
| 1-2 | LDPE-Bactenon AZ, 0.7%-Talc, 5%-TBZ, 0.2% | *S. aureus* | $9.4 \times 10^5$ | 0 | — |
| C-1 | LDPE-Bactenon AZ, 0.7%-$ZrO_2$, 2% | *S. aureus* | $9.4 \times 10^5$ | 0 | — |
| 1-BL | LDPE plate (Blank: without antimicrobial composition) | *S. aureus* | $9.4 \times 10^5$ | $3.1 \times 10^5$ | — |
| 1-3 | LDPE-Bactenon AZC, 0.5%-Talc, 1%-TBZ, 0.2% | *S. aureus* | $9.2 \times 10^5$ | $2.1 \times 10^4$ | $8.3 \times 10^2$ |
| 1-BL | LDPE plate (Blank: without antimicrobial composition) | *S. aureus* | $9.2 \times 10^5$ | $4.9 \times 10^5$ | $2.3 \times 10^5$ |

EXAMPLE 2

In this example, antimicrobial low density polyethylene (LDPE) compositions comprising antimicrobial composition at greater than 1% by weight were prepared and the antimicrobial ability thereof were measured.

Sumikasen F101-3 available from Sumitomo Chemical Co. Ltd. is used as LDPE. A predetermined amount of Bactenon AZ, TBZ and an optional titanium dioxide were mixed with the LDPE. The obtained mixture was melted and kneaded at 195°–210° C. and molded.

The moldings were cut into test pieces sized 25 mm×25 mm and 1.5 mm thick. In the test piece 2-1, Bactenon AZ containing 3.51% of Ag, 1.46% of Zn, 0.91% of Na and 1.02% of $NH_4$ and having 3.3 micro meters of Dav was used. In the test pieces 2-2, 2-3 and 2-4, Bactenon AZ containing 3.21% of Ag, 1.45% of La and 1.16% of Na and having 3.2 micro meters of Dav was used. A water content of these Bactenon was decreased below 1% by weight, before use. The result of a measurement of an antimicrobial ability is shown in the Table 2. All test pieces of the present invention show a good antimicrobial ability against *E. coli*, where the test piece 2-BL is a blank test piece containing no antimicrobial composition and it shows no antimicrobial ability.

TABLE 2

| Sample No. | Composition of molded antimicrobial polymer | Bacteria | Number of viable cells (hrs.) | | |
|---|---|---|---|---|---|
| | | | 0 | 8 | 24 |
| 2-1 | LDPE-Bactenon AZ, 2%-TBZ, 0.5% | E. Coli | $1.0 \times 10^5$ | <10 | <10 |
| 2-2 | LDPE-Bactenon AZ, 1%-TBZ, 0.2% | E. Coli | $1.0 \times 10^5$ | — | $7.6 \times 10^2$ |
| 2-3 | LDPE-Bactenon AZ, 2%-TBZ, 0.2% | E. Coli | $1.0 \times 10^5$ | <10 | <10 |
| 2-4 | LDPE-Bactenon AZ, 2%-TBZ, 0.2%-TiO$_2$, 1% | E. Coli | $1.0 \times 10^5$ | <10 | <10 |
| 2-BL | LDPE plate (Blank: without antimicrobial composition) | E. Coli | $1.0 \times 10^5$ | $6.7 \times 10^4$ | $2.2 \times 10^5$ |

EXAMPLE 3

In this example, antimicrobial polypropylene (PP) compositions were prepared and the antimicrobial ability thereof were measured.

K-1008N available from Chisso Corp., Hipole J740 available from Mitsui Petrochemical Industries, Ltd. and 7510AG available from Mitsubishi Rayon Co.,Ltd. are used as polypropylene. A predetermined amount of Bectenon having a water content below 1% by weight, TBZ, and optional zirconia, talc and cerium oxide were mixed with PP. The obtained mixture was melted and kneaded at 185°–190° C. and molded. The moldings were cut into test pieces sized 25 mm×25 mm and 1.5 mm thick.

In the test pieces 3-1, 3-2, 3-3 and 3-4, K-1008N was used as PP and Bactenon AZ containing 3.51% of Ag, 1.91% of Zn and 0.95% of Na and having 2.8 micro meters of Dav was used. All of the test pieces show a good antimicrobial ability against E. coli as represented in the Table 3A, where the test piece 3-BL is a blank test piece containing no antimicrobial composition and it shows no antimicrobial ability.

In the test piece 3-5, Hipole J740 was used as PP, while in the test pieces 3-6 and 3-7, 7510AG was used as PP, while in the test pieces 3-5 and 3-6, Bactenon AZ containing 3.62% of Ag, 2.01% of Zn and 1.12% of Na and having 2.9 micro meters of Dav was used. In the test piece 3-7, Bactenon AZC containing 3.82% of Ag, 1.13% of Zn, 1.24% of Cu and 0.89% of Na and having 3.2 micro meters of Dav was used. All of the test pieces show a good antimicrobial ability against S. aureus as represented in the Table 3B.

TABLE 3A

| Sample No. | Composition of molded antimicrobial polymer | Bacteria | Number of viable cells (hrs.) | | |
|---|---|---|---|---|---|
| | | | 0 | 8 | 24 |
| 3-1 | PP-Bactenon AZ, 2%-TBZ, 0.2% | E. Coli | $3.8 \times 10^5$ | <10 | <10 |
| 3-2 | PP-Bactenon AZ, 3%-TBZ, 0.2% | E. Coli | $3.8 \times 10^5$ | $3.6 \times 10^2$ | <10 |
| 3-3 | PP-Bactenon AZ, 3%-TBZ, 0.5% | E. Coli | $3.8 \times 10^5$ | <10 | <10 |
| 3-4 | PP-Bactenon AZ, 3%-TBZ, 0.3% ZrO$_2$, 1% | E. Coli | $3.8 \times 10^5$ | <10 | <10 |
| 3-BL | PP plate (Blank: without antimicrobial composition) | E. Coli | $3.8 \times 10^5$ | $4.1 \times 10^5$ | $3.0 \times 10^5$ |

TABLE 3B

| Sample No. | Composition of molded antimicrobial polymer | Bacteria | Number of viable cells (hrs) | |
|---|---|---|---|---|
| | | | 0 | 24 |
| 3-5 | PP-Bactenon AZ, 2%-TiO$_2$, 0.2%-TBZ, 0.2% | S. aureus | $9.2 \times 10^5$ | $5.2 \times 10^1$ |
| 3-6 | PP-Bactenon AZ, 2%-TBZ, 0.1%-Talc, 1% | S. aureus | $9.2 \times 10^5$ | <10 |
| 3-7 | PP-Bactenon AZC, 2%-TBZ, 0.5%-CeO$_2$, 1% | S. aureus | $9.2 \times 10^5$ | $7.2 \times 10^1$ |

EXAMPLE 4

In this example, antimicrobial polycarbonate (PC) compositions were prepared and the antimicrobial ability thereof was measured.

L1225W available from Teijin Kasei Corp. is used as polycarbonate. A predetermined amount of Bectenon AZ having a water content below 1% by weight, TBZ, and optional titanium dioxide were mixed with PC. The obtained mixture was melted and kneaded at 280°–290° C. and molded. The moldings were cut into test pieces sized 25 mm×25 mm and 1.5 mm thick. In this example, Bactenon AZ containing 3.57% of Ag, 1.96% of Zn and 0.95% of Na and having 2.8 micro meters of Dav was used.

The test piece C-2 is a comparative example and 4-BL is a blank test piece containing no antimicrobial composition.

The antimicrobial PC compositions of the present invention show a good antimicrobial ability against S. aureus. As both 4-2 and C-2 show a good antimicrobial ability against S. aureus, it is obvious that TBZ does not interfere an antimicrobial ability of Bactenon AZ.

TABLE 4

| Sample No. | Composition of molded antimicrobial polymer | Bacteria | Number of viable cells (hrs) | |
|---|---|---|---|---|
| | | | 0 | 24 |
| C-2 | PC-Bactenon AZ, 3%-TiO$_2$, 0.5% | S. aureus | $2.9 \times 10^5$ | <10 |
| 4-2 | PC-Bactenon AZ, 3%-TiO$_2$, 0.5%-TBZ, 0.2% | S. aureus | $2.9 \times 10^5$ | <10 |
| 4-BL | PC plate (Blank: without antimicrobial composition) | S. aureus | $2.9 \times 10^5$ | $2.0 \times 10^5$ |

EXAMPLE 5

In this example, antimicrobial ABS compositions were prepared and the antimicrobial ability thereof were measured.

TS20P available from Mitsubishi Rayon Co., Ltd. is used as ABS resin.

A predetermined amount of Bectenon AZ having a water content below 1% by weight, TBZ, and optional titanium dioxide were mixed with the ABS resin. The obtained mixture was melted and kneaded at 245°–250° C. and molded. The moldings were cut into test pieces sized 25 mm×25 mm and 1.5 mm thick. In this example, Bactenon AZ containing 3.39% of Ag, 1.93% of Zn and 1.01% of Na and having 2.9 micro meters of Dav was used.

The test piece C-3 is a comparative example.

As both of 5-2 and 5-3 show a good antimicrobial ability against *A. niger*, it is obvious that TBZ and titanium dioxide do not interfere an antimicrobial ability of Bactenon AZ.

TABLE 5

| Sample No. | Composition of molded antimicrobial polymer | Fungus | Number of viable cells (hrs.) | | |
|---|---|---|---|---|---|
| | | | 0 | 8 | 12 |
| C-3 | ABS-Bactenon AZ, 2% | A. niger | $6.7 \times 10^5$ | $8.7 \times 10^4$ | $6.5 \times 10^3$ |
| 5-2 | ABS-Bactenon AZ, 3%-TBZ, 1% | A. niger | $6.7 \times 10^5$ | $1.4 \times 10^2$ | <10 |
| 5-3 | ABS-Bactenon AZ, 2.5%-TBZ, 2%-TiO$_2$, 0.3% | A. niger | $6.7 \times 10^5$ | — | $2.4 \times 10^3$ |

EXAMPLE 6

This example is a daylight exposure test of the present antimicrobial polymer composition.

The antimicrobial polypropylene compositions were prepared in accordance with the procedure of the example 3. The compositions thereof are shown in the Table 6. The obtained moldings were cut into test pieces sized 50 mm×50 mm and 1.5 mm thick. The test pieces were exposed to sun for 6 months. In this example, Bactenon AZ containing 3.51% of Ag, 1.96% of Zn and 0.95% of Na and having 2.8 micro meters of Dav was used. A water content of the Bactenon was controlled below 1% by weight before use.

An initial color of the test pieces P-1 to P-6 were creamy white and the color did not change after the exposure test. On the other hand, a color of the comparative example C-1 changed from an initial color of white to gray with time.

An initial color of the test piece P-7 was creamy white and the color did not change after the exposure test. On the other hand, a color of the comparative example C-2 changed from an initial color of white to brown with time and became dark brown after 2 months.

An initial color of the test piece P-8 was white with pale yellow and the color did not change after the exposure test. A color of pale yellow is the color of contained TBZ. On the other hand, a color of the comparative example C-3 changed from an initial color of white to dark brown with time.

It is obvious that the antimicrobial polymer composition of the present invention has a superior discoloration resistance and weatherability to those of prior arts.

TABLE 6

| Sample No. | Composition of molded antimicrobial polymer | Initial color | Change with time after molding |
|---|---|---|---|
| P-1 | LDPE(F101-3)-Bactenon AZ, 0.7%-ZrO$_2$, 2%-TBZ, 0.5% | creamy white | no change was observed |
| P-2 | LDPE(F101-3)-Bactenon AZ, 2%-ZrO$_2$, 2%-TBZ, 0.5% | creamy white | no change was observed |
| P-3 | LDPE(F101-3)-Bactenon AZ, 0.7%-TBZ, 0.18% | creamy white | no change was observed |
| C-1 | LDPE(F101-3)-Bactenon AZ, 0.7%-ZrO$_2$, 2% | white | color changed to gray and a degree of the coloring became stronger with time |
| P-4 | LDPE(F101-3)-Bactenon AZ, 2%-Talc, 5%-TBZ, 0.5% | creamy white | no change was observed |
| P-5 | LDPE(F101-3)-Bactenon AZ, 2%-TiO$_2$, 1%-TBZ, 0.3% | creamy white | no change was observed |
| P-6 | LDPE(F101-3)-Bactenon AZ, 0.7%-CeO$_2$, 1%-TBZ, 0.5% | creamy white | no change was observed |
| P-7 | PP(J740)-Bactenon AZ, 2%-TBZ, 0.5% | creamy white | no change was observed |
| C-2 | PP(J740)-Bactenon AZ, 2% | white | color changed to brown with time and became dark brown after two months |
| P-8 | PP(7510AG)-Bactenon AZ, 2%-TBZ, 0.5%-TiO$_2$, 0.5% | creamy white | no change was observed |
| C-3 | PP(7510AG)-Bactenon AZ, 2% | white | color changed to brown with time and became dark brown after two months |

EXAMPLE 7

This example shows that the antimicrobial composition contained in the antimicrobial polymer composition of the present invention does not interfere a mildewcidal ability of TBZ.

The antimicrobial LDPE composition was prepared in accordance with the procedure of the example 1 employing Sumikasen F101-3 as LDPE. The antimicrobial LDPE composition comprises 3% by weight of Bactenon AZ and 0.4% by weight of TBZ. The obtained moldings were cut into test pieces sized 50 mm×50 mm and 1.5 mm thick. In this example, Bactenon AZ containing 3.51% of Ag, 1.96% of Zn and 0.95% of Na and having 2.8 micro meters of Dav was used. A water content of the Bactenon was controlled below 1% by weight before use. For a blank test, the sample without Bactenon was prepared.

A measurement of mildewcidal ability was carried out in accordance with the procedure defined in the Japanese Industrial Standard (JIS Z 2911) and described in the following.

1) The tested fungus

*Aspergillus niger* (IFO 4407)

*Penicillium funiculosum* (IFO-6345)

*Chaetomium globosum* (IFO-6347)

*Gliocladium virens* (IFO-6355)

*Aureobasidium pulluland* (IFO-6353)

2) Preparation of the suspension of the tested fungus

Each of the fungi was cultivated in a potato dextrose agar medium until enough spores were obtained. Each of the fungi was suspended in sterile 0.005% dioctyl sodium sulfosuccinate aqueous solution and form a suspension of each fungus. The same amount of each suspension was mixed to prepare a suspension of mixed spores.

3) Procedure of the test a) A sample was put in a laboratory dish and spray the suspension of mixed spores to wet a surface of the sample in accordance with the JIS methods.

b) The dish was kept at 29° C. and relative humidity 85% for 30 days. A growth of mycelium was visually observed. The result is shown in the Table 7.

It is obvious from the result that the antimicrobial composition contained in the antimicrobial polymer composition of the present invention does not interfere a mildewcidal ability of TBZ.

TABLE 7

| Composition of molded antimicrobial polymer | Result |
|---|---|
| LDPE-Bactenon AZ, 3%-TBZ, 0.4% | No growth of mycelium was observed at all of four surfaces of the test pieces |
| LDPE-Blank (without antimicrobial composition) | A growth of mycelium was observed at all of four surfaces of the test pieces |

I claim:

1. An antimicrobial polymer composition comprising
   (1) a thermoplastic synthetic polymer;
   an amount of an antimicrobial composition having an antimicrobial coat of an aluminosilicate on the surface of silica gel, wherein said aluminosilicate contains antimicrobial metal ions, and
   and an amount of thiabendazole,
   wherein the amount of said antimicrobial composition is at least 0.2% by weight of the antimicrobial polymer composition and wherein the amount of thiabendazole is at least 0.03% by weight of the antimicrobial composition.

2. An antimicrobial polymer composition of claim 1 wherein said antimicrobial metal ions are silver ions and one or two optional metal ions selected from the group consisting of zinc ions and copper ions.

3. An antimicrobial polymer composition of claim 2, wherein a content of the silver ions is at least 0.3% by weight of the antimicrobial composition.

4. An antimicrobial polymer composition of claim 1 further comprising at least one additive selected from the group consisting of titanium dioxide, zirconium oxide, cerium oxide and layer silicate.

5. An antimicrobial composition of claim 1 wherein said thermoplastic synthetic polymer is selected from the group consisting of polyethylene, polypropylene, polycarbonate and ABS resins.

6. An antimicrobial polymer composition consisting essentially of
   (a) thermoplastic synthetic polymer;
   (b) a content of antimicrobial composition of at least 0.2% by weight of the antimicrobial polymer composition wherein said antimicrobial composition is silica gel and an antimicrobial coat of aluminosilicate on the surface of the silica gel and wherein said aluminosilicate contains antimicrobial metal ions;
   (c) a content of thiabendazole of at least 0.03% by weight of the antimicrobial composition; and
   (d) optionally at least one additive selected from the group consisting of titanium dioxide, zirconium oxide, zirconium oxide, cerium oxide and layer silicate.

7. An antimicrobial composition of claim 6 wherein said thermoplastic synthetic resin is selected from the group consisting of polyethylene, polypropylene, polycarbonate and ABS resins.

* * * * *